United States Patent
Imbert et al.

(10) Patent No.: US 9,737,314 B1
(45) Date of Patent: Aug. 22, 2017

(54) BROACH HANDLE WITH BIAS ATTACHMENT

(71) Applicant: Greatbatch Medical S.A., Clarence, NY (US)

(72) Inventors: Christian Imbert, Evillard (CH); Michael F. Scalise, Clarence, NY (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 15/350,410

(22) Filed: Nov. 14, 2016

(51) Int. Cl.
*A61B 17/00* (2006.01)
*A61B 17/16* (2006.01)

(52) U.S. Cl.
CPC *A61B 17/1659* (2013.01); *A61B 2017/00367* (2013.01); *A61B 2017/00464* (2013.01); *A61B 2017/00469* (2013.01); *A61B 2017/00477* (2013.01)

(58) Field of Classification Search
CPC ...... A61B 17/1659; A61B 2017/00367; A61B 2017/00464; A61B 2017/00469; A61B 2017/00477
USPC ................. 403/1, 43–48; 433/102–114, 135, 433/146–147; 606/1, 79–85
See application file for complete search history.

(56) References Cited

U.S. PATENT DOCUMENTS

| | | | |
|---|---|---|---|
| 4,021,918 A | 5/1977 | Bailey et al. | |
| 4,582,489 A | 4/1986 | Listl et al. | |
| 4,765,328 A | 8/1988 | Keller et al. | |
| 5,089,003 A | 2/1992 | Fallin et al. | |
| 5,443,471 A | 8/1995 | Swajger | |
| 5,496,323 A | 3/1996 | Dye et al. | |
| 5,529,495 A | 6/1996 | Edwards et al. | |
| 5,584,803 A | 12/1996 | Stevens et al. | |
| 7,637,909 B2 | 12/2009 | Lechot et al. | |
| 7,976,545 B2 | 7/2011 | Hershberger et al. | |
| 7,988,699 B2 | 8/2011 | Martz et al. | |
| 2004/0075432 A1 | 4/2004 | Loud et al. | |
| 2004/0127888 A1 | 7/2004 | O'Neil et al. | |
| 2011/0092963 A1 | 4/2011 | Castro et al. | |
| 2012/0071862 A1 | 3/2012 | Burgi et al. | |

OTHER PUBLICATIONS

Collet, Wikipedia, Collet, Jul. 12, 2010, http://en.wikipedia.org/wiki/Collet, Jul. 12, 2010.
Spring Steel, Wikipedia, Spring steel, Aug. 30, 2010, http://en.wikipedia.org/wiki/Spring_steel, Aug. 30, 2010.
Wikipedia, Collet, Jul. 7, 2016, http://en.wikpedia.org/wiki/Collet, Jul. 7, 2016.

*Primary Examiner* — Gary Jackson
*Assistant Examiner* — Jonathan Kuo
(74) *Attorney, Agent, or Firm* — Michael F. Scalise (57) ABSTRACT

A surgical tool handle for holding, securing and portioning orthopedic tools is described. The surgical tool handle having a tool attachment mechanism comprising a bias member connected to an actuator. The bias member is positioned within a distal end opening within the handle. Rotation of the actuator causes rotation of the bias member such that when a connection member of a tool, such as a broach, rasp or other cutting tool, is positioned within an opening of the bias member, the bias member wraps around and tightens onto the connection member. Rotating the actuation cable in an opposite direction rotates the bias member in the opposite direction, which thereby releases the tool connection member, and the tool, from the handle.

28 Claims, 4 Drawing Sheets

BROACH HANDLE WITH BIAS ATTACHMENT

BACKGROUND OF THE INVENTION

1. Field of the Invention

The present invention relates to surgical tool handles for use in orthopedic implant surgery. More particularly, the present invention relates to a tool handle apparatus having a bias member mechanism for securing a surgical tool to a tool handle.

2. Prior Art

Surgical cutting tools are extensively used during orthopedic surgical procedures. Surgical tools such as broaches, rasps and other cutting devices are often used to prepare a patient's bone, such as during hip arthroplasty. For example, during a hip arthroplasty procedure, a surgeon may use a broach to prepare the inner surfaces of the intramedullary canal of a patient to receive a femoral hip prosthesis. This preparation of the intramedullary canal by the surgeon is designed to insure a proper fit between the patient's femur and the prosthesis.

However, regardless of the surgical procedure, it is important for a surgical tool to remain in a secure relationship to its handle. During a surgical procedure, mechanical forces and stresses are often applied to the connection points of these tools. Thus, connections between the tool and handle are sometimes prone to misalignment or even potential failure.

Various mechanisms have been used to attach a surgical tool to a handle. Examples of these mechanisms include a locking pawl mechanism disclosed in U.S. patent application Pub. No. 2012/0071862 to Burgi and the coil spring locking post assembly disclosed in U.S. Pat. No. 5,089,003 to Fallin et al.

In the '003 patent, a locking mechanism comprising a locking key 50 and a coil spring 52 is disclosed. As discussed by Fallin, a proximal end of a cutter 14 is positioned within an access opening 44 of the handle 12. Once positioned within the access opening 44, a locking key 50 which is compressed by a spring coil 56, is sprung into a "V" shaped notch 30 of the proximal end of the cutter 14. Thus, as the proximal end is positioned within the opening, the bias force of the coil spring 56 forces the locking key 50 within the notch, thereby locking the cutter 14 within the handle 12. The cutter 14 is released from the handle by drawing the locking post 50 in a proximal direction out from the notch, thereby freeing the cutter 14 from the handle 12. The locking post 50 is drawn in a proximal direction by use of a cable 70 that is connected to the locking post 50. Thus, as the cable 70 is drawn in a proximal direction, it moves the locking post 50 in a proximal direction, and out of the notch of the tool.

In U.S. patent application Pub. No. 2012/0071862, Burgi discloses a locking pawl 58 that pivotally positions an extending hook 68 in and out of a locking indentation 78A. Actuation of a lever arm causes the locking pawl 58 to pivotally position the hook end of the pawl in and out of the locking indentation 78A thus, securing a tool to the handle.

However, in contrast to the prior art, the tool handle of the present invention provides a bias member attachment mechanism that secures a surgical tool, such as a broach, rasp or cutting device to a handle. In the present invention, a tool connection member is positioned within the bias member, such as a coil spring, residing within the distal end of the handle. Actuation of the bias member, by an actuator, tightens the bias member around the connection member, thus securing the tool to the handle.

Thus, by constricting the bias member along a length of the connection member, a secure connection between the tool and the handle can be achieved. In contrast, the attachment mechanisms of the prior art have primarily relied on a point contact connection wherein the end of a hook or locking key provides the connection between the tool and the handle. The connection mechanism of the present invention provides a length of a bias member that wraps around a tool connection member, providing a greater contact area between the tool and handle and thus, a more robust connection is provided.

In addition, the reduced number of components comprising the bias member connection mechanism of the present invention provides a cost effective means of securing a surgical tool to a handle. Furthermore, the bias member connection of the present invention is also more conducive to manufacturing.

SUMMARY OF THE INVENTION

The present invention provides an improved surgical tool handle apparatus for use with an orthopedic tool, such as a broach, rasp or other cutting tool used to prepare a patient's bone for a prosthesis implant. The device provides a handle body having a distal end portion with a connection end adapted for removably connecting to a surgical tool.

In a preferred embodiment, an attachment mechanism comprising a bias member and an actuator resides within the handle. More specifically, the bias member resides in an opening disposed through the distal end of the handle body for receiving a portion of a surgical tool there within. The actuator having a length extending from a proximal actuator end to a distal actuator end is connected to the bias member. In a preferred embodiment, the distal end of the actuator is connected to a proximal end of the bias member and the opposing proximal end of the actuator extends proximally away from the bias member, and at least partially within the tool handle. The distal end of the bias member is secured to the handle. This distal end connection can be by an outwardly extending protrusion of the bias member received in a handle slot or by an adhesive connection between the bias member and the handle.

Connection between the surgical tool and the handle is achieved by positioning a tool connection member, such as the post of a rasp, within an opening of the bias member residing at the distal end of the handle. The actuator is then rotated to thereby cause the bias member to also rotate. Continued rotation of the bias member by the actuator causes the bias member to tighten around the connection member or post of the surgical tool, thereby securing the tool to the distal end of the handle. The tool may be removed from the handle by rotating the actuator in the opposite direction used to secure the tool to the handle.

DETAILED DESCRIPTION OF THE PREFERRED EMBODIMENTS

Figure 1:
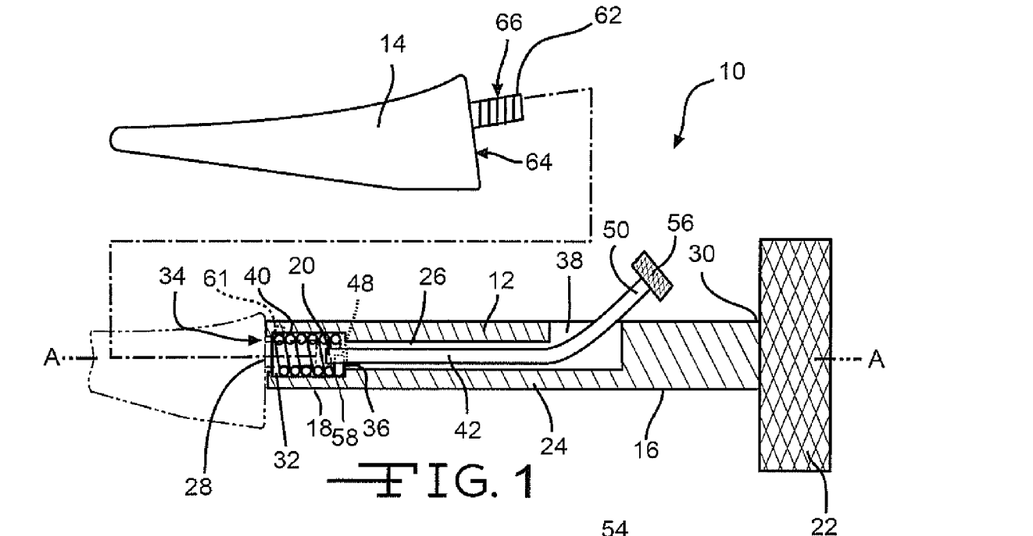
FIG. 1 illustrates a cross-sectional view of an embodiment of a tool handle apparatus of the present invention.
Figure 3:
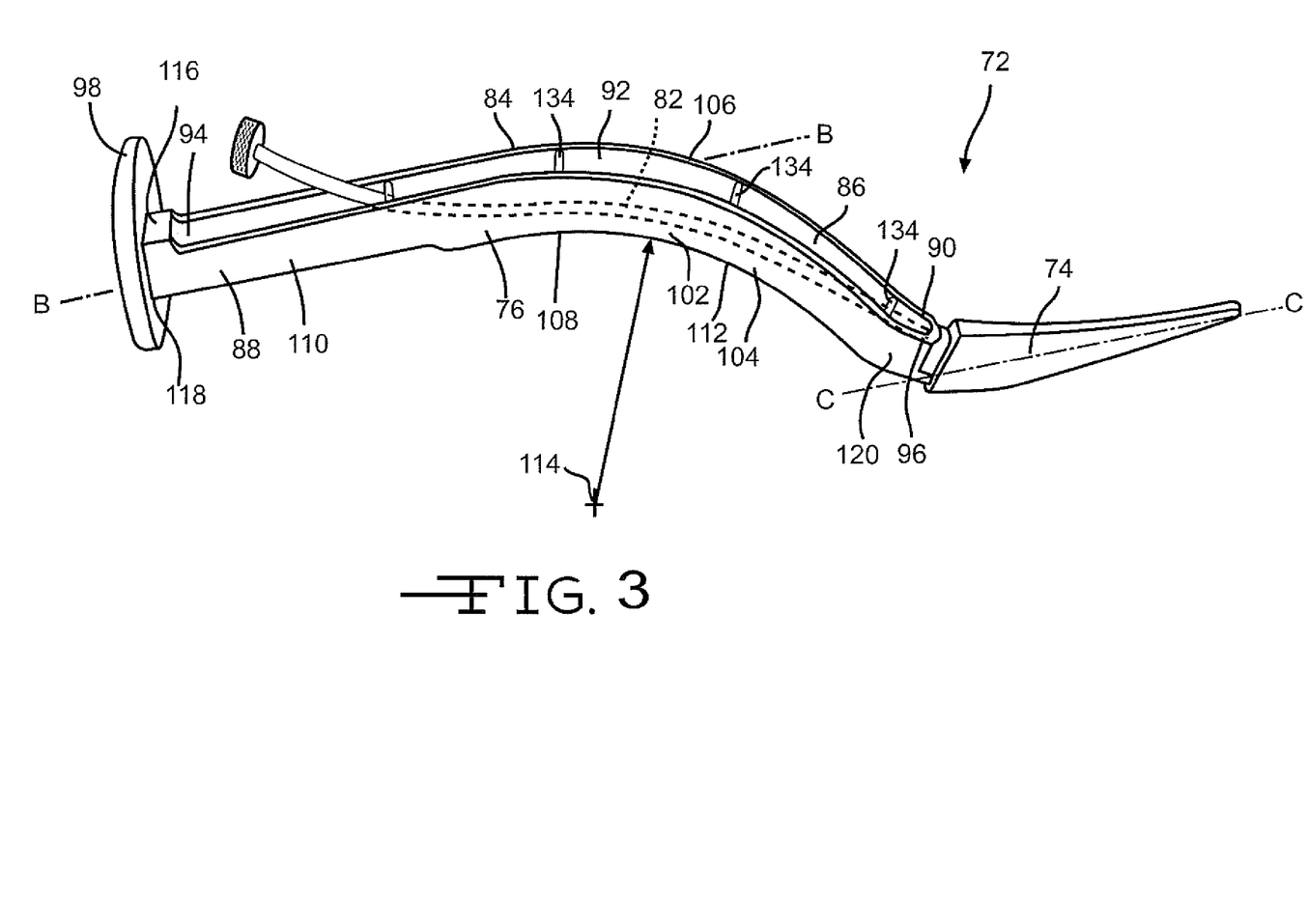
FIG. 3 shows a perspective view of an alternate embodiment of a tool handle apparatus according to the present invention.
Figure 5:
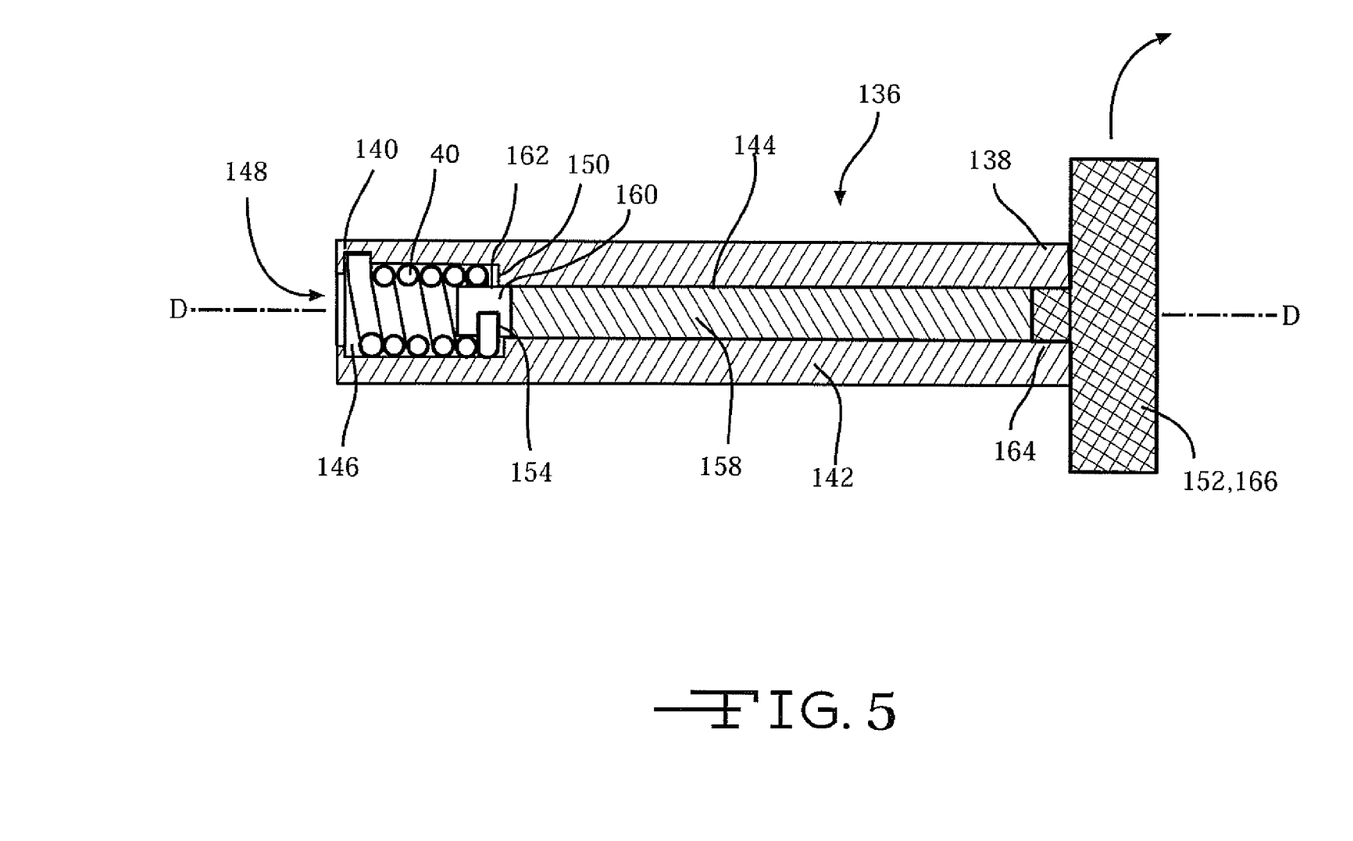
FIG. 5 illustrates a cross-sectional view of an alternate embodiment of a tool handle of the present invention.

Turning now to the drawings, FIGS. 1, 3 and 5, illustrate various embodiments of a tool handle and apparatus according to the present invention. Each of the various embodiments of the handle apparatus comprises a surgical tool attachment mechanism having a bias member and an actuator. The bias member is designed to wrap around and tighten a connection member of a surgical tool, such as a post of a broach, rasp or other cutting tool to thereby secure the tool to the handle.

FIG. 1 illustrates an embodiment of a surgical tool handle apparatus 10, for example a broach handle, of the present invention. In addition to the broach handle shown in FIG. 1, the tool handle apparatus 10 of the present invention may be used to secure a variety of surgical tools including but not limited to a rasp, a reamer or cutting device.

Figures 4, 4A:
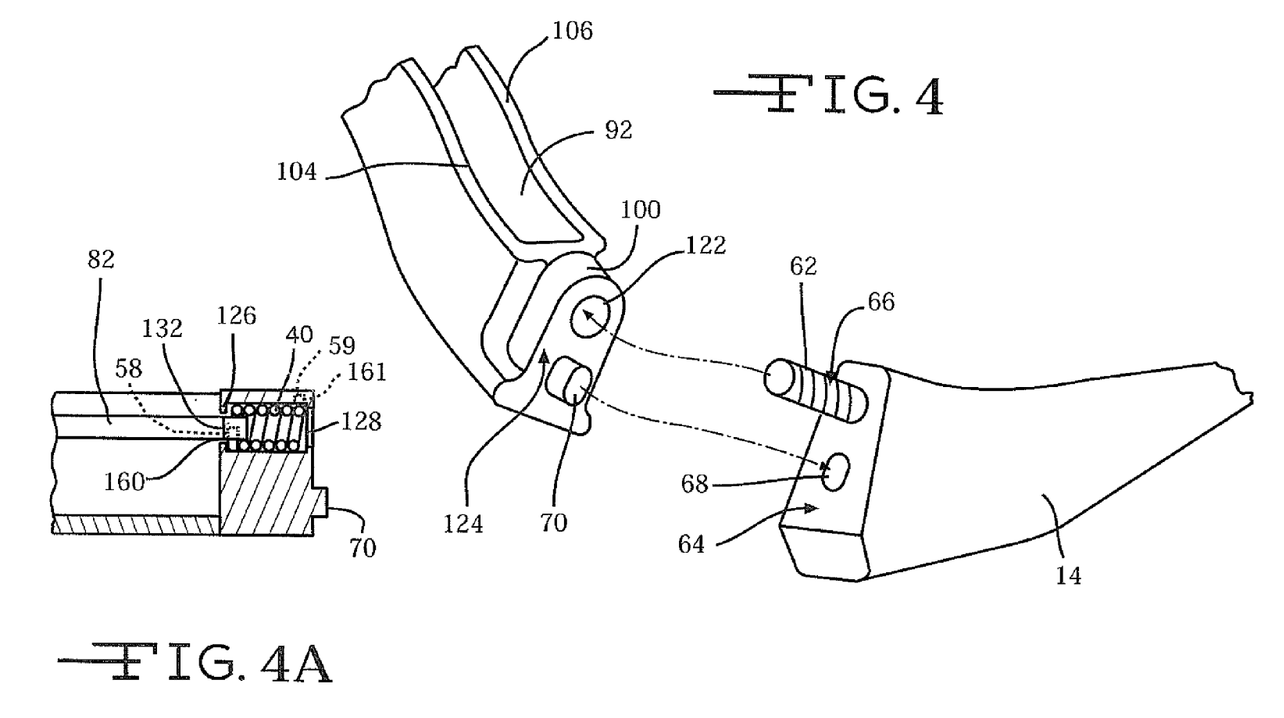
FIG. 4 shows a magnified view of an embodiment illustrating the attachment of an orthopedic tool to the distal end of the tool handle shown in FIG. 3.
FIG. 4A is a cross-sectional view of the distal tool handle end shown in FIG. 5.

The illustrated surgical tool handle apparatus 10 comprises a body 12 and a surgical tool 14, such as the broach tool illustrated in FIGS. 1, 3 and 4. The handle body 12 comprises a length that extends along a longitudinal axis A-A from a proximal handle portion 16 to a distal handle portion 18. In a preferred embodiment, a surgical tool attachment mechanism 20 at least partially resides within the distal portion 18 of the handle 12. A strike plate 22 may reside at the proximal portion 16 of the handle 12.

In a preferred embodiment, as shown in FIG. 1, the handle body 12 comprises an annular handle sidewall 24 which surrounds a lumen 26. The lumen 26 extends at least part way between a distal end 28 and a proximal end 30 within the handle 12. The lumen 26 may extend through the distal end 28 of the handle elongate body 12. A socket portion 32 of the lumen 26 preferably resides within the distal portion 18 of the handle body 12. As illustrated, the socket portion 32 has a distal socket opening 34 that extends through the distal end 28 of the handle 12. The distal socket opening 34 is spaced apart from a proximal socket opening 36. In a preferred embodiment, a diameter of the socket portion 32 may be greater than a diameter of the remainder of the lumen 26. In an embodiment, the components of the attachment mechanism 20 of the present invention at least partially reside within the socket portion 32 of the lumen 26.

As illustrated, the lumen 26 preferably extends longitudinally within the handle body 12 from the proximal socket opening 36 of the socket lumen to a position distal of the strike plate 22. A side access opening 38 is positioned within the proximal portion 16 of the handle 12. The side access opening 38 preferably extends through the sidewall 24 of the handle body 12 such that it is connected to the lumen 26.

Figure 2:
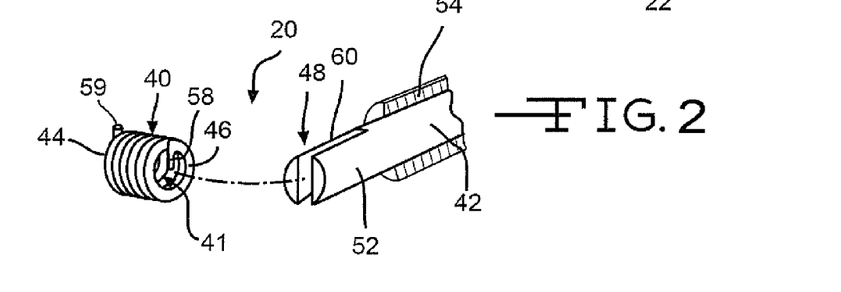
FIG. 2 illustrates a magnified perspective view of an embodiment of a bias member and distal actuator end of the present invention.
Figure 2A:
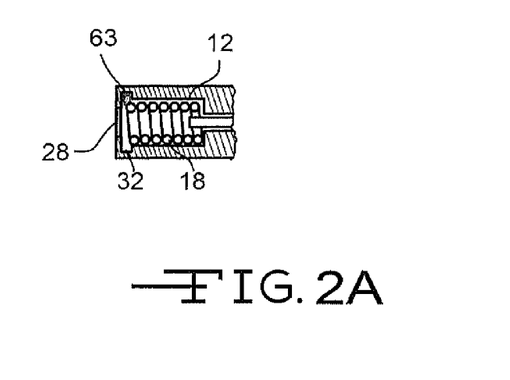
FIG. 2A is a cross-sectional view of the distal tool handle end showing a distal end of the bias member secured to the handle using an adhesive or weld 63.

In a preferred embodiment, the attachment mechanism 20 comprises a bias member 40 and an actuator or actuator assembly 42. In a preferred embodiment, the bias member 40 comprises a coil spring having a lumen 41. As shown in FIGS. 1 and 2, the bias member 40 comprises opposing distal and proximal bias member ends 44, 46 and resides within the socket portion 32 of the handle lumen 26.

The actuator 42, having a length extending from a distal actuator end 48 to a proximal actuator end 50, is at least partially positioned within the lumen 26 of the handle body 12. The distal actuator end 48 is connected to the bias member 40 and the proximal actuator end 50 resides at the proximal portion 16 of the handle 12. In a preferred embodiment, the actuator 42 may comprise a cable, a rod or series of interconnected linkage members. It is noted that an actuator is preferably a single component that acts on and enables rotation of the bias member 40, whereas, an actuator assembly is preferably a plurality of components, for example interconnected linkage members, that work together to act on and enable rotation of the bias member 40.

As shown in FIG. 2, in a preferred embodiment, the actuator 42 may comprise an inner core 52 that is positioned within an outer sleeve 54. More specifically, the inner core 52 is connected to the proximal bias member end 46. An actuator knob 56 is connected to the inner core 52 at a proximal end thereof. In a preferred embodiment, rotation of the knob 56 rotates the inner core 52 within the sleeve 54 of the actuator 42. Since the distal end 48 of the inner core 52 is connected to the proximal end 46 of the bias member 40, rotation of the knob 56 also rotates the bias member 40. As illustrated in FIG. 1, the actuator 42 extends from the socket portion 32 of the lumen, through the access opening 38 to reside external of the handle sidewall 24.

In a preferred embodiment, as shown in FIG. 2, the proximal end 46 of the bias member 40 comprises a first protrusion 58 that extends radially inwardly towards the imaginary longitudinal axis A-A. The first protrusion 58 is preferably positioned within a slot 60 that extends across a diameter and within a portion of the distal end of the inner core 52 of the actuator 42. A distal end of the bias member 40 has a second protrusion 59 (FIG. 2) that extends radially outwardly away from the longitudinal axis A-A. The second protrusion 59 is positioned or received is a radial slot 61 (FIG. 1) in the handle 12. The bias member protrusions 58, 59, actuator slot 60 and handle slot 61 connections enable the actuator 42 to rotate the bias member 40 either in a clockwise or counter clockwise direction.

FIG. 2B illustrates an alternate embodiment where an adhesive or weld 63 connects the distal coil end to the elongate handle body 12. If a weld, it is preferably a laser weld.

The surgical tool 14 such as the broach illustrated in FIGS. 1, 3, and 4, preferably comprises a connection member 62. As defined herein, a connection member is a portion of a surgical tool that is secured within the handle 12. A connection member 62 may comprise a post, a flange, or extension that extends outwardly from the tool 14. As illustrated, the connection member 62 extends outwardly from a proximal end surface 64 of the broach 14. In a preferred embodiment, the connection member 62 may have a connection member exterior surface 66 that is roughened or knurled. In addition, the connection member 62 is preferably dimensioned such that it is positionable within the socket portion 32 of the lumen residing at the distal portion 18 of the handle 12. More preferably, the connection member 62 of the tool 14 is dimensioned to be positionable within a lumen 41 that extends lengthwise within the bias member 40.

As will be described in detail hereinafter, in the preferred embodiment of the present invention with the bias member being a coil spring 40, rotation of the actuator 42 in one of the clockwise or counter clockwise directions causes coil spring to enlarge its coil lumen from a relaxed state having a first diameter to a second diameter of a size sufficient to receive the connection member of a surgical tool through the distal coil open end and into the coil lumen. Then, rotation of the actuator 42 in a second, opposite direction causes rotation of the coil spring 40 to constrict the coil lumen from the second diameter to a lesser, third diameter perpendicular to the longitudinal axis that is sufficient to securely contact the connection member and thus secure the surgical tool 14 to the surgical tool handle 12.

As shown in FIG. 4, the tool 14 may also comprise a tool alignment opening 68. This tool alignment opening 68 preferably corresponds with a handle alignment pin 70 that extends from the distal end 28 of the handle 12. The handle alignment pin 70 is designed to be positionable within the tool alignment opening 68 of the tool 14.

In a preferred embodiment, the elongate housing body 12 may be constructed from a polymeric or metallic material. Furthermore, the components of the attachment mechanism 20 may also be composed of a polymeric or metallic material.

In operation, the tool connection member 62 is positioned within the distal end of the handle 12. More preferably, the connection member 62 is positioned within the socket portion 32 of the lumen 26. Most preferably, the connection member 62 is positioned within the lumen 41 of the bias member 40 such that a portion of a length of the connection member 62 extends there within. Once correctly positioned, the actuator 42 is either rotated in a clockwise or counter-clockwise manner. In a preferred embodiment, the actuator knob 56 is rotated to thereby cause rotation of the actuator 42 and bias member 40. In a preferred embodiment, as the bias member 40 is rotated around the connection member 62, the bias member 40 wraps around and becomes in a tightened relationship with the connection member 62, thereby securing the tool 14 to the handle 12.

In a preferred embodiment, the tool 14 may be removed from the handle 12. In this embodiment, the actuator 42 is rotated in an opposite direction used to previously tighten the bias member 40 to the connection member 62. For example, if the bias member 40 is wrapped around the connection member 62 in a clockwise manner, the actuator 42 is rotated in a counter clockwise manner to loosen the bias member 40 from the connection member 62. Once the connection between the bias member 40 and the connection member 62 is loosened, the tool 14 can be removed from the handle 12.

FIG. 3 illustrates an alternate embodiment of a tool and handle apparatus 72 of the present invention. As illustrated, the apparatus 72 comprises a surgical tool 74, i.e. a broach, a rasp, or cutting blade and a tool handle 76. Similarly to the embodiment shown in FIG. 1, the surgical tool and handle apparatus 72 shown in FIG. 3 has a bias member 40 (FIG. 4A) and an actuator or actuator assembly 82. However, unlike the embodiment shown in FIG. 1, the tool handle 76 shown in FIG. 3 comprises a housing sidewall 84 having an opening 86 that extends through an upper portion of the sidewall 84. As illustrated, the opening 86 extends along an upper portion of the housing sidewall 84 from a proximal handle portion 88 to a distal handle portion 90. The opening 86 thereby provides a channel 92 that extends from a proximal channel end 94 to a distal channel end 96. The channel 92 allows for a more thorough cleaning of the tool handle 76 as cleaning agents can more easily access within the interior of the handle 76.

As shown in FIG. 3, the handle 76 has a handle length that extends from a strike plate 98 that may be positioned at the proximal handle portion 88 to a distal neck portion 100 (FIG. 4) positioned at the distal channel end 96. An intermediate handle housing portion 102 resides therebetween. In a preferred embodiment, the intermediate housing portion 102 comprises spaced apart right and left housing sidewalls 104 and 106 extending upwardly from a housing bottom wall 108 to the upper opening 86. A feature of the present handle assembly 72 is that the intermediate housing portion 102 is further comprised of an axial housing region 110 aligned along longitudinal axis B-B and a curved housing region 112. As particularly shown in FIG. 3, the curved housing region 112 provides the sidewalls 104, 106 with a radius of curvature that is centered about a focal point 114. In a preferred embodiment, the radius of curvature of the curved housing region 112 may range from about 1 cm to about 10 cm.

The curved housing region 112 may curve in either a leftward direction or a rightward direction. This construction provides the intermediate portion 102 with a generally U-shaped cross-section perpendicular to axis B-B and along the curvature of the curved region 112 extending from the proximal housing portion 88. The bottom wall 108 is preferably planar along the proximal housing portion 88 and the intermediate housing portion 102. In addition, the intermediate housing portion 102 may also curve in a downwardly or upwardly direction along the curved region 112 as well.

The intermediate housing portion 102 seamlessly meets the proximal housing portion 88. In a preferred embodiment, the proximal housing portion 88 may have a generally rectangular shaped cross-section, perpendicular to the axis B-B, provided by the right and left sidewalls 104, 106 and bottom sidewall 108. Alternatively, the cross-section of the intermediate housing portion 102 is not limited to a rectangular shape but may also have a curved, round or hexagonal shaped cross-section. The sidewalls 104, 106 may also be contoured to provide a finger grip region. The strike plate 98 may be connected to an end of the proximal housing portion 118. A ledge 116 may be positioned distal of the strike plate 98.

As illustrated in FIG. 3, the curved region 112 of the intermediate housing portion 102 preferably extends in a downwardly direction until it meets the distal neck region 120 which is preferably aligned along a second longitudinal axis C-C. Longitudinal axis C-C is parallel to, but spaced from longitudinal axis B-B. In that manner, the right and left side walls 104, 106 forming the intermediate housing portion 102 seamlessly extend distally and downwardly to form the distal neck region 120 of the housing.

At the end of the distal neck region 120, the right and left side walls 104, 106 meet the nose 100 (FIGS. 4 and 4A). The handle alignment post 70 positioned vertically below a nose opening 122 preferably extends outwardly from an exterior nose surface 124. The handle alignment post 70 is designed to be positionable within the tool alignment opening 68 and the tool connection member or post 62 is designed to be positionable within the nose opening 122.

As shown in FIG. 4A, a socket lumen portion 126 resides within the nose 100 of the distal end 96 of the tool handle 76. Like the previous tool handle embodiment 12, the socket lumen 126 comprises a distal socket opening 128 spaced from a proximal socket opening 130. In a preferred embodiment, the bias member is a coil spring 40 that resides within the socket lumen 126. An actuator slot 160 at a distal end 132 of the actuator 82 is connected to the bias member 40 in a similar manner as described with respect to the tool handle assembly 10. The coil spring 40 also has an outwardly extending radial protrusion 59 that is positioned or received is a radial slot 161 in the handle 76 in a similar manner as describe with respect to the tool handle assembly 10. The bias member protrusions 58, 59, actuator slot 160 and handle slot 161 connections enable the actuator 82 to rotate the bias member 40 either in a clockwise or counter clockwise direction to thereby selectively connect and disconnect the toll handle 76 from the connection member of a surgical tool. Furthermore, actuator or assembly 82 may comprise a cable, a rod or a series of interconnected linkages.

The actuator 82 is preferably positioned lengthwise within the channel 92 of the handle 76. A series of bars 134 preferably extend across the width of the handle 76 preventing the actuator 82 from coming out of the channel 92. In addition, the bars 134 minimize obstruction to the opening 86 such that the handle 76 and the channel 92 may be easily cleaned.

FIG. 2B illustrates an alternate embodiment where an adhesive or weld 63 connects the distal coil end to an elongate handle body, which in this embodiment is the tool handle 76. If a weld, it is preferably a laser weld.

Another alternate embodiment of a tool handle 136 of the present invention is provided in FIG. 5. As illustrated, the tool handle 136 comprises a handle length extending along longitudinal axis D-D from a proximal handle end 138 to a distal handle end 140. The handle 136 preferably comprises an annular sidewall 142 that surrounds a lumen 144. A socket portion 146 of the lumen 144 comprises a distal socket opening 148 spaced from a proximal socket opening 150. The socket portion 146 resides at the distal handle end 140. A strike plate 152 may reside at the proximal handle end 138.

A connection mechanism comprising a bias member 40 and an actuator or actuator assembly 158 resides within the handle 136. More specifically, the bias member 40 preferably resides within the socket lumen portion 146 and the actuator 158 preferably resides within the lumen 144. In a preferred embodiment, a distal end 160 of the actuator 158 is connected to a proximal, inwardly extending protrusion 58 of the bias member 40 and a proximal actuator assembly end 164 is connected to the strike plate 152 or an actuator knob 166. A distal end 132 of the actuator 82 is connected to the bias member 80. Similar to the previous embodiments, the bias member 40 may comprise a coil spring having an outwardly extending protrusion 59 that is positioned or received is a radial slot in the handle 136. The bias member protrusions 58, 59, actuator assembly slot and handle slot connections enable the actuator 158 to rotate the bias member 40 either in a clockwise or counter clockwise direction to selectively connect and disconnect the tool handle 136 from a surgical tool in a similar manner as previously described with respect to FIGS. 1 to 4, 4A and 4B.

In a preferred embodiment, the strike plate 152 or knob 166 of tool handle 136 is capable of rotating in either a clockwise or counterclockwise manner. Thus, as the strike plate 152 is rotated, so too is the bias member 40 positioned within the socket lumen portion 146 at the distal handle end 140. Furthermore, actuator 158 may comprise a cable, a rod or a series of interconnected linkages.

FIG. 2B illustrates an alternate embodiment where an adhesive or weld 63 connects the distal coil end to an elongate handle body, which in this embodiment is the tool handle 136. If a weld, it is preferably a laser weld.

Of course, the forgoing description is that of certain features, aspects and advantages of the present invention, to which various changes and modifications can be made without departing from the spirit and scope of the present invention. Moreover, the handle tool apparatus need not feature all of the objects, advantages, features and aspects discussed above. Thus, for example, those of skill in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or sub-combinations of these specific features and aspects of embodiments may be made and still fall within the scope of the invention. Accordingly, it should be understood that various features and aspects of embodiments may be made and still fall within the scope of the invention. Accordingly, it should be understood that various features and aspects of the disclosed embodiments can be combined with or substituted for one another in order to form varying modes of the discussed tool handle apparatus.

What is claimed is:

1. A surgical tool handle, comprising:
   a) an elongate body extending from a proximal body portion to a distal body portion;
   b) a body lumen at least partially residing within the elongate body, wherein the body lumen extends from a proximal body lumen end residing in the proximal body portion to a distal body lumen portion having a distal body lumen end residing in the distal body portion;
   c) a coil spring positioned within the distal body lumen portion, wherein the coil spring has a coil lumen extending along a longitudinal axis from a proximal coil end to a distal coil end, the coil lumen having a first diameter perpendicular to the longitudinal axis with the coil spring in a relaxed state, and wherein the distal coil end is connected to the elongate body; and
   d) an actuator extending through the body lumen, the actuator comprising spaced apart proximal and distal actuator ends, wherein the distal actuator end is received inside the proximal coil end to thereby connect the actuator to the coil spring while leaving open a remainder of the coil spring lumen extending distally from the distal actuator end to the distal coil end, and wherein the proximal actuator end is accessible from outside the body adjacent to the proximal body portion,
   e) wherein rotation of the actuator in a first direction causes rotation of the coil spring to enlarge the coil lumen from the relaxed state having the first diameter to a second diameter of a size sufficient to receive the connection member of a surgical tool through the distal coil open end and into the coil lumen, and wherein rotation of the actuator in a second, opposite direction causes rotation of the coil spring to constrict the coil lumen from the second diameter to a lesser, third diameter perpendicular to the longitudinal axis that is sufficient to securely contact the connection member and thus secure the surgical tool to the surgical tool handle.

2. The surgical tool handle of claim 1 wherein the first and third diameters of the coil lumen are less than the second diameter of the coil lumen, and wherein the first and third diameters are either the same or the third diameter is greater than the first diameter, but less than the second diameter.

3. The surgical tool handle of claim 1 wherein the proximal coil end comprises an inwardly extending protrusion received in a slot at the distal end of the actuator.

4. The surgical tool handle of claim 1 wherein the distal coil end has an outwardly extending protrusion that is received in a slot in the elongate body to connect the coil spring to the elongate body.

5. The surgical tool handle of claim 1 wherein an adhesive or weld connects the distal coil end to the elongate body.

6. The surgical tool handle of claim 1 wherein the coil lumen of the coil spring is configured to securely contact the connection member of a surgical tool selected from the group consisting of a broach, a reamer, a rasp and a cutting device.

7. The surgical tool handle of claim 1 wherein the actuator is selected from the group consisting of a cable, a rod, a series of interconnected linkage members, and combinations thereof.

8. The surgical tool handle of claim 1 wherein a strike plate resides at a proximal end of the proximal body portion.

9. The surgical tool handle of claim 1 wherein the distal body lumen portion has a lumen diameter perpendicular to the longitudinal axis that is greater than the coil spring having the second diameter of the coil lumen.

10. The surgical tool handle of claim 1 wherein the elongate body is composed of a material selected from the group consisting of a polymer, a metal, and a combination thereof.

11. A surgical tool apparatus, comprising:
  a) a surgical tool handle comprising:
    i) an elongate body extending from a proximal body portion to a distal body portion;
    ii) a body lumen at least partially extending within the elongate body, wherein the body lumen extends from a proximal body lumen end residing in the proximal body portion to a distal body lumen portion having a distal body lumen end residing in the distal body portion;
    iii) a coil spring residing within the distal body lumen portion, wherein the coil spring has a coil lumen extending along a longitudinal axis from a proximal coil end to a distal coil end, the coil lumen having a first diameter perpendicular to the longitudinal axis with the coil spring in a relaxed state, and wherein the distal coil end is connected to the elongate body; and
    iv) an actuator extending through the body lumen, the actuator comprising spaced apart proximal and distal actuator ends, wherein the distal actuator end is received inside the proximal coil end to thereby connect the actuator to the coil spring, and wherein the coil spring lumen extends distally from the distal actuator end to the distal coil end, and wherein the proximal actuator end is accessible from outside the body adjacent to the proximal body portion;
  b) a surgical tool comprising a tool connection member positionable within the distal body lumen portion; and
  c) wherein the actuator is rotatable in a first direction to enlarge the coil lumen from the relaxed state having the first diameter to a second diameter of a size that is sufficient to receive the connection member of the surgical tool through the distal coil open end and into the coil lumen, and wherein rotation of the actuator in a second, opposite direction causes rotation of the coil spring to constrict the coil lumen from the second diameter to a lesser, third diameter perpendicular to the longitudinal axis that is sufficient to contact the connection member and thus secure the surgical tool to the surgical tool handle.

12. The surgical tool handle of claim 11 wherein the first and third diameters of the coil lumen are less than the second diameter of the coil lumen, and wherein the first and third diameters are either the same or the third diameter is greater than the first diameter, but less than the second diameter.

13. The surgical tool apparatus of claim 11 wherein the proximal coil end comprises an inwardly extending protrusion received in a slot at a distal end of the actuator.

14. The surgical tool apparatus of claim 11 wherein the distal coil end has an outwardly extending protrusion that is received in a slot in the elongate body to connect the coil spring to the elongate body.

15. The surgical tool apparatus of claim 11 wherein an adhesive or weld connects the distal coil end to the elongate body.

16. The surgical tool apparatus of claim 11 wherein the coil lumen of the coil spring is configured to securely contact the connection member of a surgical tool selected from the group consisting of a broach, a reamer, a rasp, and a cutting device.

17. The surgical tool apparatus of claim 11 wherein the actuator is selected from the group consisting of a cable, a rod, a series of linkage members, and combinations thereof.

18. The surgical tool apparatus of claim 11 wherein the proximal coil end comprises a radial protrusion received in a distal slot at the distal end of the actuator.

19. The surgical tool apparatus of claim 11 wherein a strike plate resides at a proximal end of the proximal body portion.

20. A surgical tool handle, comprising:
  a) an elongate housing comprising a bottom sidewall extending to upwardly opposing left and right sidewalls to thereby form a housing channel at least partially extending from a proximal housing end to a nose lumen located at a distal housing portion;
  b) a coil spring positioned within the nose lumen, wherein the coil spring has a coil lumen extending along a longitudinal axis from a proximal coil end to a distal coil end, the coil lumen having a first diameter perpendicular to the longitudinal axis with the coil spring in a relaxed state, and wherein the distal coil end is connected to the elongate body;
  c) an actuator extending through the housing channel, the actuator comprising spaced apart proximal and distal actuator ends, wherein the distal actuator end is received inside the proximal coil end to thereby connect the actuator to the coil spring, and wherein the coil spring lumen extends distally from the distal actuator end to the distal coil end, and wherein the proximal actuator end is accessible from outside the housing adjacent to the proximal housing end,
  d) wherein rotation of the actuator in a first direction causes rotation of the coil spring to enlarge the coil lumen from the relaxed state having the first diameter to a second diameter of a size sufficient to receive the connection member of a surgical tool through the distal coil open end and into the coil lumen, and wherein rotation of the actuator in a second, opposite direction causes rotation of the coil spring to constrict the coil lumen from the second diameter to a lesser, third diameter perpendicular to the longitudinal axis that is sufficient to securely contact the connection member and thus secure the surgical tool to the surgical tool handle.

21. The surgical tool handle of claim 20 wherein the first and third diameters of the coil lumen are less than the second diameter of the coil lumen, and wherein the first and third diameters are either the same or the third diameter is greater than the first diameter, but less than the second diameter.

22. The surgical tool handle of claim 20 wherein the proximal coil end comprises a inwardly extending protrusion received in a slot at a distal end of the actuator.

23. The surgical tool handle of claim 20 wherein the distal coil end has an outwardly extending protrusion that is received in a slot in the elongate body to connect the coil spring to the elongate body.

24. The surgical tool handle of claim 20 wherein an adhesive or weld connects the distal coil end to the elongate body.

25. The surgical tool handle of claim 20 wherein the coil lumen of the coil spring is configured to securely contact the connection member of a surgical tool selected from the group consisting of a broach, a rasp and a cutting device.

26. The surgical tool handle of claim 20 wherein a curved housing region resides between the proximal housing end and the distal housing portion having the nose lumen.

27. The surgical tool handle of claim 26 wherein the curved housing region has a radius of curvature ranging from 1 cm to 10 cm.

28. The surgical tool handle of claim 20 wherein a strike plate resides at the proximal housing end.

* * * * *